US010226174B2

(12) United States Patent
Cornsweet et al.

(10) Patent No.: US 10,226,174 B2
(45) Date of Patent: Mar. 12, 2019

(54) OCULAR FUNDUS IMAGING SYSTEMS, DEVICES AND METHODS

(71) Applicant: Brien Holden Vision Institute, Sydney (AU)

(72) Inventors: Tom N. Cornsweet, Prescott, AZ (US); Paul Peterson, Prescott, AZ (US); Kenneth W. Chapman, Raleigh, NC (US); Frank George Evans, Portland, OR (US)

(73) Assignee: Brien Holden Vision Institute, Sydney (AU)

( * ) Notice: Subject to any disclaimer, the term of this patent is extended or adjusted under 35 U.S.C. 154(b) by 0 days.

(21) Appl. No.: 14/916,886

(22) PCT Filed: Sep. 5, 2014

(86) PCT No.: PCT/US2014/054307
§ 371 (c)(1),
(2) Date: Mar. 4, 2016

(87) PCT Pub. No.: WO2015/035175
PCT Pub. Date: Mar. 12, 2015

(65) Prior Publication Data
US 2016/0213249 A1  Jul. 28, 2016

Related U.S. Application Data

(60) Provisional application No. 61/874,651, filed on Sep. 6, 2013.

(51) Int. Cl.
*A61B 3/14* (2006.01)
*A61B 3/12* (2006.01)
(Continued)

(52) U.S. Cl.
CPC .............. *A61B 3/12* (2013.01); *A61B 3/0025* (2013.01); *A61B 3/0091* (2013.01); *A61B 3/14* (2013.01); *A61B 3/152* (2013.01)

(58) Field of Classification Search
CPC ........... A61B 3/14; A61B 3/12; A61B 3/0025; A61B 3/0075; A61B 3/0091
(Continued)

(56) References Cited

U.S. PATENT DOCUMENTS 3,460,887 A * 8/1969 Grolman .............. A61B 3/1225
351/206
4,715,703 A  12/1987 Cornsweet et al.
(Continued)

FOREIGN PATENT DOCUMENTS

CN  1951314 A  4/2007

OTHER PUBLICATIONS

International Search Report dated Dec. 24, 2014 for PCT/US2014/054307.

*Primary Examiner* — Mahidere S Sahle
(74) *Attorney, Agent, or Firm* — Jones Day

(57) ABSTRACT

A fundus camera for photographing a fundus of an eye that includes a plurality of light sources with differing frequencies for illuminating the fundus, a plurality of fixation lights configured to orient the fundus in varying positions, and an imaging sensor. The fundus camera further includes at least one processor configured to cause the illumination of the plurality of light sources and the plurality of fixation lights in a predetermined pattern to obtain a plurality of narrow bandwidth images of the fundus and to manipulate and stitch the resulting narrow bandwidth images into a composite color image.

22 Claims, 5 Drawing Sheets

(51) Int. Cl.
*A61B 3/00* (2006.01)
*A61B 3/15* (2006.01)

(58) Field of Classification Search
USPC .......................................................... 351/206
See application file for complete search history.

(56) References Cited

U.S. PATENT DOCUMENTS

| | | |
|---|---|---|
| 2003/0025877 A1 | 2/2003 | Yancey et al. |
| 2003/0058405 A1 | 3/2003 | Cornsweet et al. |
| 2007/0030451 A1 | 2/2007 | Ishihara et al. |
| 2010/0049057 A1 | 2/2010 | Gellerman et al. |
| 2011/0091083 A1 | 4/2011 | Liu et al. |
| 2012/0044458 A1 | 2/2012 | Iwanga |
| 2012/0224142 A1 | 9/2012 | Cornsweet et al. |
| 2012/0287255 A1 | 11/2012 | Ignatovich et al. |
| 2013/0182217 A1 | 7/2013 | Cheng et al. |
| 2013/0215385 A1 | 8/2013 | Hirose |

\* cited by examiner

FIG. 3
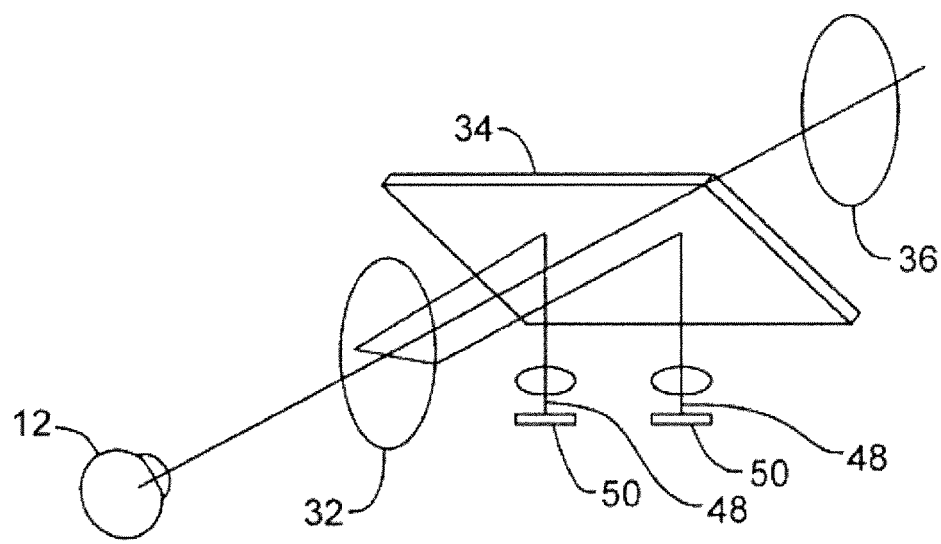
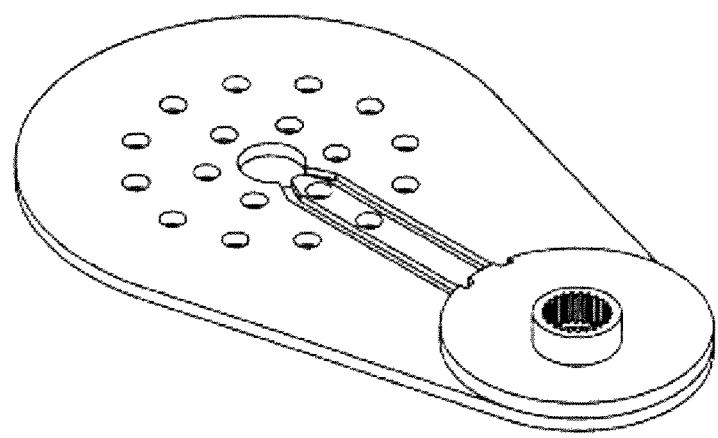
FIG. 4

OCULAR FUNDUS IMAGING SYSTEMS, DEVICES AND METHODS

CROSS-REFERENCE TO RELATED APPLICATIONS

This application is the National Phase application of International Application No. PCT/US2014/054307, filed Sep. 5, 2014, which designates the United States and was published in English, and which claims priority to U.S. Provisional Application No. 61/874,651, filed on Sep. 6, 2013, the content of which is herein incorporated, in its entity, by reference.

This application is also related to U.S. application Ser. No. 13/409,056, filed on Feb. 29, 2012; International Application No. PCT/US2012/027161, filed on Feb. 29, 2012; and U.S. Provisional Application No. 61/448,342, filed Mar. 2, 2011. Each of these applications, in its entirety, is herein incorporated by reference.

TECHNICAL FIELD

This document generally relates to ocular fundus imaging systems, devices, and methods. More specifically, this disclosure relates to ocular fundus imaging systems, devices and methods for photographing portions of the fundus of an eye and creating a composite image of the fundus in substantially real time.

BACKGROUND

The inside back surface of the eye, which contains the retina, blood vessels, and neural tissue, is called the ocular fundus. Many systemic pathologies, as well as ocular pathologies, cause changes in the appearance of the ocular fundus. As a consequence, virtually all ophthalmic exams and most general physical exams include observation of the fundus. This observation is most often performed using a device called an ophthalmoscope, a hand-held device that provides the observer with a magnified direct view through the patient's pupil.

There are a number of factors that can limit the usefulness of an ophthalmoscope examination. For example, many ophthalmoscopes have rather poor optical resolution, limiting the detail that is visible by the ophthalmoscope. Additionally, the patient's eye is constantly moving which causes the scene through the ophthalmoscope to shift continuously, making it difficult to observe any fundus detail. Further, the ophthalmoscope is not capable of creating a permanent record of the exam (e.g., an image of the fundus).

In an attempt to overcome these difficulties, cameras for fundus imaging were developed. For example, a typical modern fundus camera collects digital color images of regions of the fundus. These cameras are expensive and difficult to operate from an operator's standpoint. For example, to collect an image of the fundus with a typical fundus camera, a number of steps are undertaken. The patient looks toward the camera at a target. The operator adjusts the camera to achieve an acceptable image. For example, the operator may adjust the brightness of the illumination and/or the alignment of the optical system with respect to the patient's pupil, etc. To perform these steps with a cooperative patient typically requires extensive practice and experience. Imaging patients who are unable to hold their gaze or their eyes or head steady, or to understand the instructions, is even more difficult. As a result, these cameras often take poor quality images which may not be useful to observe patient pathologies.

Accordingly, what is desired are ocular fundus imaging systems, devices, and methods that alleviate, overcome, or at least reduce, one or more of these problems.

SUMMARY OF EMBODIMENTS

Exemplary embodiments may provide a fundus camera for photographing a fundus of an eye, the fundus camera comprising: a plurality of light sources with differing wavelengths for illuminating the fundus; a plurality of fixation lights configured to orient the fundus in varying positions; an imaging sensor; and at least one processor configured to cause the illumination of the plurality of light sources and the plurality of fixation lights in a predetermined pattern, to obtain a plurality of monochromatic images of the fundus, and to manipulate and stitch the resulting monochromatic images into a composite image. In exemplary embodiments, the composite image may be a color image.

In exemplary embodiments, the predetermined pattern may be to sequentially illuminate one of the plurality of light sources with a corresponding one of the plurality of fixation lights until at least one image has been obtained for substantially all of the combinations of light source and fixation lights.

In exemplary embodiments, the monochromatic images may be stereo images.

In exemplary embodiments, the plurality of light sources may comprise any combination of an IR LED, a red LED, a green LED and/or a blue LED.

In exemplary embodiments, the fundus camera may comprise, 2, 3, 4, 5, 6, 7, 8, 9, 10, 11, 12, 13, 14, or 15 fixation lights.

In exemplary embodiments, the processor may be configured to analyze at least one monochromatic image in substantially real time to determine whether a replacement image is required.

In exemplary embodiments, the image stitching may be performed, at least in part, by calculating a variance of the pixels in a pixel matrix in an image and comparing a cross-correlation to an adjacent image to determine an overlap.

In exemplary embodiments, the imaging sensor may have a field of view of less than 15, 20, 25, 30, 35, 40, 45, or 50 degrees.

In exemplary embodiments, the fundus camera may be configured to detect a cataract by quantifying the amount of light scatter in the lens of the eye.

In exemplary embodiments, the fundus camera may further comprise a baffle movable from a position in which the baffle covers more than a first half of the pupil to a position where the baffle covers more than a second half of the pupil and then to a position where the baffle is completely removed from the optical path to enable the at least one processor to differentiate back scatter from forward scatter.

In exemplary embodiments, the fundus camera may be configured to perform an auto-refraction.

Exemplary embodiments may provide a fundus camera for photographing a fundus of an eye, the fundus camera comprising: an optical path; at least one imaging sensor; an assembly comprising an IR light source, a red light source, and a green light source, wherein the assembly is configured to be movable in at least one axis so as to be individually alignable with the optical path to obtain images of the fundus; a plurality of fixation lights configured to orient the fundus in varying positions as a result of a eye's changed direction of gaze; and a processor configured to control the fundus camera such that, in exemplary embodiments, the fundus camera may automatically obtain a composite image of the fundus by: orienting the IR light source with the optical axis of the camera; illuminating the plurality of fixation lights sequentially; obtaining monochromatic (or narrow bandwidth) images of the fundus corresponding to the plurality of fixation lights; orienting the red light source with the optical axis; illuminating the plurality of fixation lights sequentially; obtaining monochromatic (or narrow bandwidth) images of the fundus corresponding to the plurality of fixation lights; orienting the green light source with the optical axis; illuminating the plurality of fixation lights sequentially; obtaining monochromatic (or narrow bandwidth) images of the fundus corresponding to the plurality of fixation lights; and stitching the resulting monochromatic (or narrow bandwidth) images into a composite image of the fundus.

Exemplary embodiments may provide a fundus camera for photographing a fundus of an eye, the fundus camera comprising: an optical path; at least one imaging sensor; an assembly comprising an IR light source, a red light source, and a green light source, wherein the assembly is configured to be movable in at least one axis so as to be individually alignable with the optical path to obtain images of the fundus; a plurality of fixation lights configured to orient the fundus in varying positions as a result of a eye's changed direction of gaze; and a processor configured to control the fundus camera such that during operation the fundus camera may automatically obtain a composite image of the fundus by: illuminating a first of the plurality of fixation lights; orienting the IR light source, the red light source, and the green light source with the optical axis, sequentially; obtaining at least one monochromatic (or narrow bandwidth) image of the fundus corresponding to each of the IR light source, the red light source, and the green light source; illuminating a next of the plurality of fixation lights; orienting the IR light source, the red light source, and the green light source with the optical axis, sequentially; obtaining at least one monochromatic (or narrow bandwidth) image of the fundus corresponding to each of the IR light source, the red light source, and the green light source; and stitching the resulting monochromatic (or narrow bandwidth) images into a composite image of the fundus.

In exemplary embodiments, the fundus camera may be configured to measure pallor by: selecting a field of the composite image; for each of the plurality of pixels within the field, calculating pallor as K*(R−G)/(R+G), wherein R is the value of a particular pixel obtained while the fundus was illuminated by the red light source or IR light source and G is the value of a corresponding pixel obtained while the fundus was illuminated by the green light source; and displaying the resulting image as a pseudocolored image.

In exemplary embodiments, the fundus camera may be configured to measure the shape of the cupping of the optic disk by: selecting a field of the composite image comprising the optic disk; for each of the plurality of pixels within the field, calculating pallor as (R−G)/(R+G), wherein R is the value of a particular pixel obtained while the optical axis was illuminated by the red light source or IR light source and G is the value of a corresponding pixel obtained while the optical axis was illuminated by the green light source; determining the outline of the cupping of the optic disk as the portion of the image where the pallor transitions from being less than a predetermined threshold to being greater than a predetermined threshold; and displaying the resulting outlined portion of the image.

In exemplary embodiments, the fundus camera may be configured to measure macular pigment density by: identifying a first image that includes the macula under IR illumination, identifying a second image that includes the macula under green illumination; computing the intensity of the infrared image divided by the intensity of the green image for each pixel within the images; and displaying the resulting ratios as a pseudocolored image map.

DESCRIPTION OF THE DRAWINGS

Exemplary embodiments will now be described, by way of example only, with reference to the accompanying drawings in which:

FIG. 3 is a schematic diagram of an exemplary implementation of a pupil camera for use with a device for imaging an ocular fundus;

FIG. 4 is an exemplary embodiment of a reticle for use with exemplary embodiment of a device for imaging an ocular fundus;

DETAILED DESCRIPTION OF EXEMPLARY EMBODIMENTS

The exemplary embodiments described herein include a number of optical elements or components, many of which, as individual elements, may be conventional in at least one of construction and/or operation. These components, we appreciate, may be incorporated, properly collaboratively combined, in modified embodiments of the system of the invention, with these components possessing a wide variety of recognized, readily user-chooseable, and fully satisfactory, optical characteristics. Accordingly, details of these several elements, except to the extent believed necessary to convey a clear understanding of how the systems, devices, and methods perform, may not be discussed in detail. Rather, the disclosure will rely appropriately on the knowledge and skill of those generally skilled in the art of optics, and on the below-described, fully-informative operational description of systems, devices, and methods, as being entirely adequate to enable those skilled in the art to build and use the exemplary embodiments.

Figure 1:
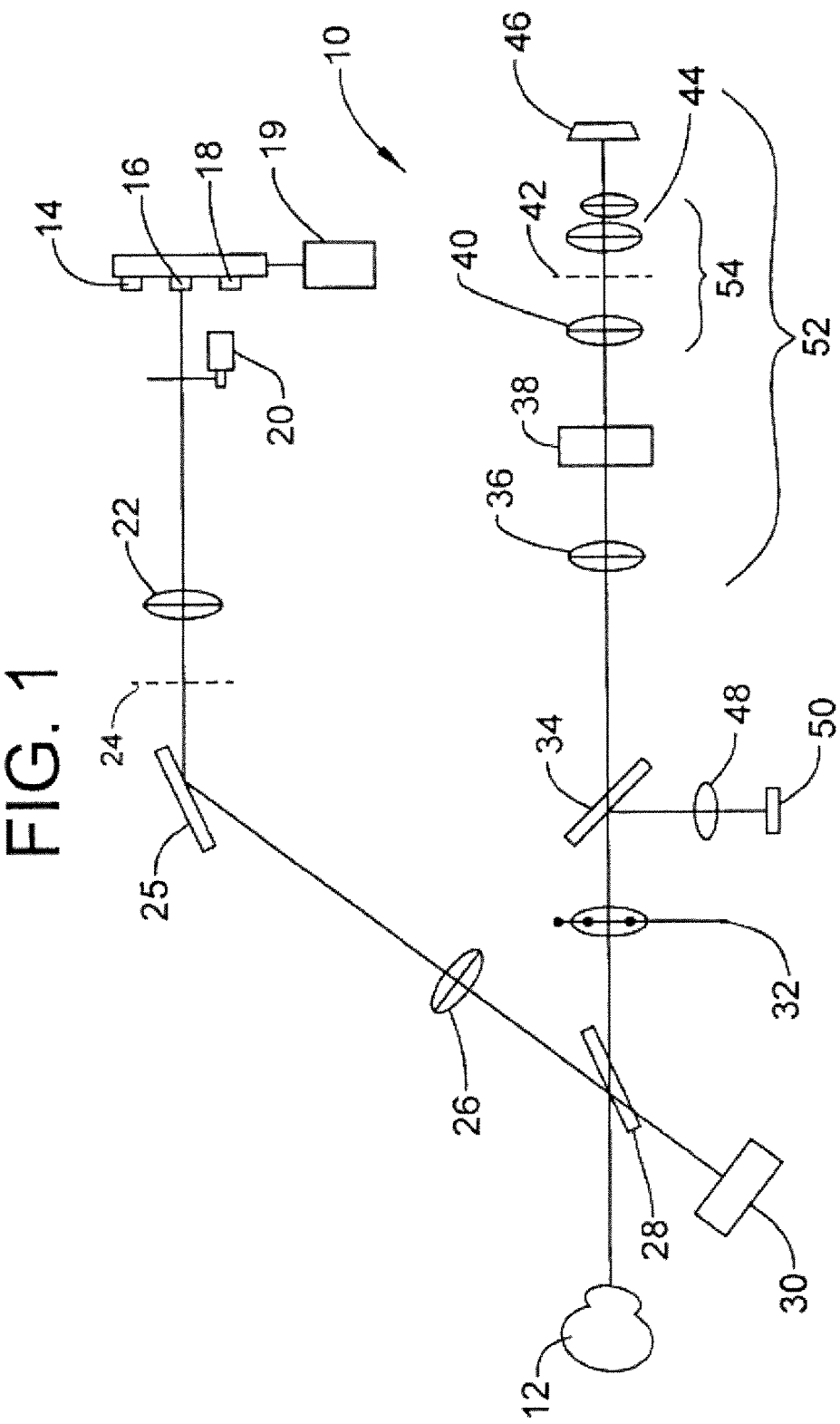
FIG. 1 is a schematic diagram of an exemplary device for use in imaging an ocular fundus.
Figure 2:
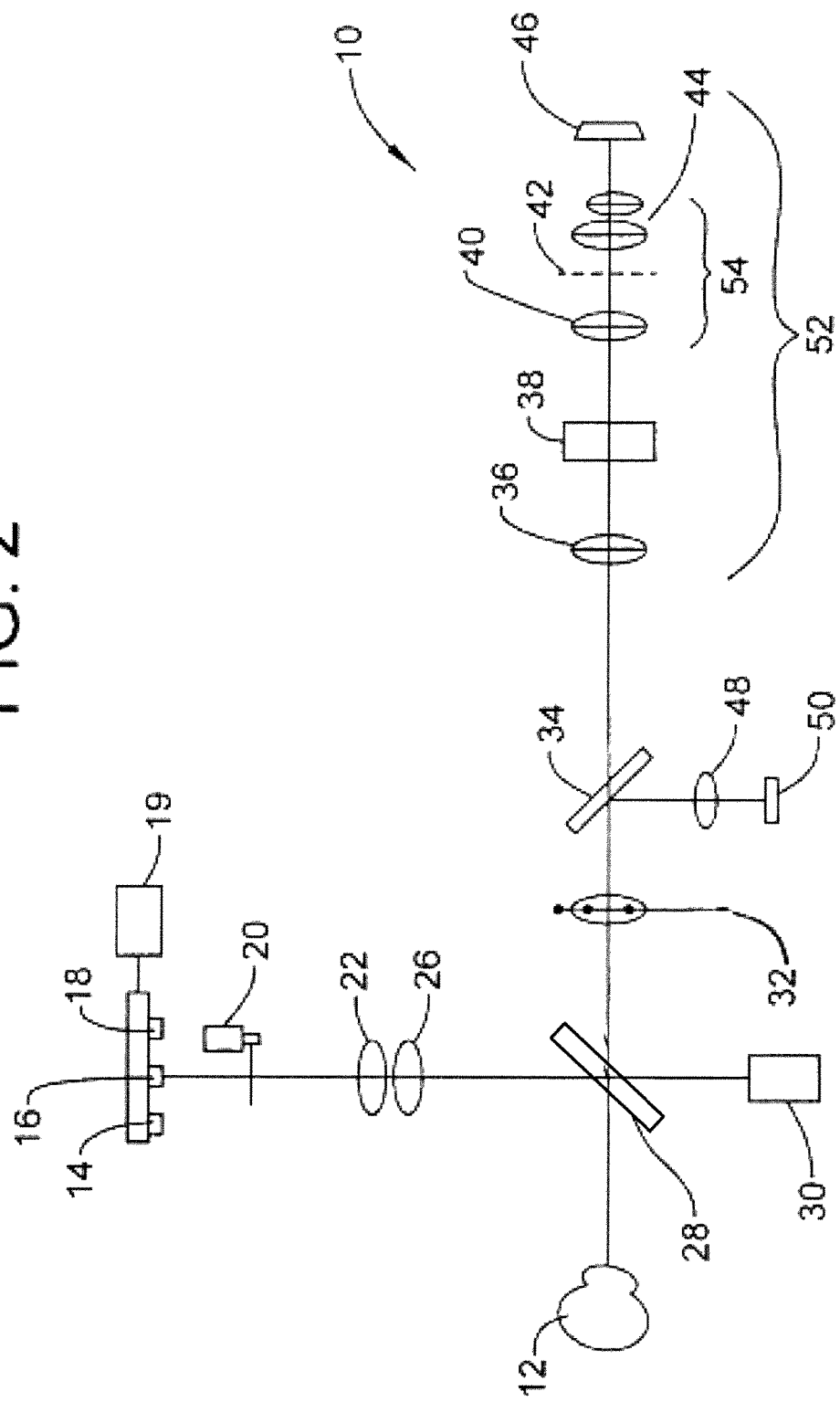
FIG. 2 is a schematic diagram of another exemplary device for use in imaging an ocular fundus.

FIG. 1 is a schematic diagram of an exemplary device for use in imaging an ocular fundus. FIG. 1 includes a camera 10 configured to image an eye 12. The camera 10 comprises a plurality of LEDs. For example, as shown in FIG. 1, the LEDs may comprise a red LED, 14, a green LED, 16, and an IR LED 18. In exemplary embodiments, as shown in FIG. 1, the LEDs may be mounted to a linear actuator 19 (or a similar mechanism) to move the LEDs into the optical path individually. The LEDs are configured to transmit light toward and then through a focus plate, 20, lens 22 and a mirror 25. The light is then reflected by a mirror 25 towards lens 26. In exemplary embodiments, the camera may not include the mirror 25. For example, in some embodiments, the pathway from the LEDS 14, 16, 18 to the lens 26 may not need to be bent. For example, the path may progress entirely downward as illustrated in FIG. 2 which is a schematic diagram of another exemplary device for use in imaging an ocular fundus that does not comprise the mirror 25. After the light passes through lens 26 it reaches beam splitter 28 which is configured to direct a portion of the light toward the eye 12 and the remaining portion of the light towards a light trap 30. Lens 22 is configured to collimate the light from the LED light source and lens 26 is configured to image the LED light in the pupil of the eye 12. The light passing through the pupil of the eye 12 illuminates a region (e.g., a circular or substantially circular region) of the fundus. In exemplary embodiments, the diameter of the region may be about 15, 20, 25, or 30 degrees in diameter.

Some of the light that enters the pupil of the eye is ultimately reflected from the fundus and reaches the beam splitter 28. At the beam splitter 28, a portion (e.g., about half) of the reflected light passes through to lens 32, beam splitter 34, lens 36, and parallel plane shifter 38. Then the reflected light passes through camera lens 54 which may comprise a lens 40 and an aperture 42. Ultimately, the image is captured by an image sensor 46. Lens 32 is configured to collimate the light from the patient's pupil and lens 36 is configured to image the pupil in the plane of aperture 42.

At the same time, the light reflected from the fundus is acted upon by the optics of the patient's eye to form an image of the fundus in the space between lens 32 and lens 36.

In exemplary embodiments, lens 36, parallel plane shifter 38, lens 40, aperture 42, lens 44, and sensor 46 may all be mounted together on a single carriage that may be moved axially by e.g., a lead-screw and motor. In exemplary embodiments, the arrangement of these elements may be referred to as a fundus focus assembly 52. In exemplary embodiments, the image of the fundus may be focused on the sensor 46 by moving the assembly 52 until the image of the fundus is in front of the focal plane of lens 36 which collimates the light from the fundus. In exemplary embodiments, the aperture 42 may be located in the back of the focal plane of lens 36, and therefore the image of the patient's pupil is conjugate with aperture 42. In exemplary embodiments, the entire optical system may be configured to be movable in three dimensions to align to the pupil of the patient. In exemplary embodiments, the movement of the system may be accomplished with one or more motors.

FIG. 3 is a schematic diagram of an exemplary implementation of a pupil camera for use with a device for imaging an ocular fundus. In exemplary embodiments, a portion (e.g., 2%, 5%, 7%, or 10%) of the light arriving at beam splitter 34 may be reflected downward towards a pair of lenses 48 and pupil cameras 50. As illustrated in FIG. 3, the lenses 48 may comprise a pair of lenses and the cameras 50 may comprise a corresponding pair of cameras. Accordingly, in exemplary embodiments, an image of the patients pupil may be imaged on the two cameras 50. For example, in exemplary embodiments, the pupil image on one pupil camera may provide a signal to move the optical system of the camera vertically and/or horizontally to center the pupil on the optical axis of the instrument. Then, the second camera may image the same pupil, but as if looked at from a different angle, to provide a signal for moving the optical system toward or away from the eye to focus the image of the IR, red, and/or green LEDs.

In exemplary embodiments, in operation, the operator may enter patient information using an interface provided on a computer screen. The patient may be seated in front of the device, and the operator may instruct the patient to position his head in an appropriate manner to look into the instrument at e.g., a small flashing light. Once the patient is correctly positioned, an image of the patient's pupil may appear in a window on the operator's screen, and the operator may manipulate the display until the pupil is properly positioned in the display. For example, in exemplary embodiments, the operator may use a mouse to drag the image of the pupil until it is approximately centered in the window.

In exemplary embodiments, dragging or moving the mouse horizontally may drive a motor that moves the system horizontally, and dragging the mouse towards or away from the operator may cause the system to move up or down. In this manner, the operator interacts with the system to accomplish the coarse manual alignment of the optical system to the pupil. In exemplary embodiments, instead of a mouse, the operator may interact with the system via a touch screen. In exemplary embodiments, after the coarse alignment is completed, the pupil appears as a bright disk, illuminated by infrared light reflected from the fundus (alternatively, in exemplary embodiments, the infrared light may illuminate the general area of the eye while the pupil camera sees a dark pupil). In exemplary embodiments, the operator may then initiate the imaging process by e.g., pressing a button labeled—Take Images—. At this stage, the remaining image collection procedure follows automatically (or semi-automatically).

In exemplary embodiments, in operation, the region of the fundus for imaging is identified. In exemplary embodiments, the patient may be asked to look at a particular light source (e.g., a spot of light within their field of view). When a patient looks at the spot of light, what is actually happening is that optics of the patient's eye form an image of the spot somewhere on the fundus. When the patient looks at the spot, the patient rotates their eye, which causes the retina to slide under the image of the spot until that image falls on a particular region of the fundus called the fovea. In exemplary embodiments, the device 10 may comprise a plurality of fixation lights. For example, in exemplary embodiments, the device may comprise seven fixation lights. Alternatively, in embodiments, the number of fixation lights may be 2, 3, 4, 5, 6, 7, 8, 9, 10, 11, or 12. In exemplary embodiments, the fixation lights may be located at or around lens 32 and/or lenses 48. For example, in exemplary embodiments, the device may comprise a centrally located blue LED between the lenses 48 and six peripheral LEDs located at or near lens 32. In exemplary embodiments, the LED located between the lenses 48, may be at an optical distance from lens 32 such that the LED lies in the back focal plane of lens 32. Therefore, light from that central LED is collimated as it arrives at the patient's eye and is therefore approximately (or substantially) in focus. Its rays also travel along the optical axis of the main optical system and therefore the LED appears to be centered in the system, and on the fundus, its image is centered on the region of the fundus that may be illuminated by LED light sources 14, 16, 18. Further, because the optical axis of the system containing lenses 22 and 26 is, after the action of beam-splitter 28, coincident with the axis of the part of the system containing lenses 32, 36, and 54, the region of the fundus that is imaged by the overall system is the same as the region illuminated by LED light sources 14, 16, 18. Therefore, when the central fixation LED is illuminated and when the patient looks at it, the region of the fundus that is imaged is centered on the patient's fovea.

To image a different region of the fundus, a different internal fixation LED may be turned on, e.g., one located laterally from the optical axis. For example, in exemplary embodiments where there may be seven fixation LEDs in the instrument, located at different positions around and/or on the optical axis, seven different regions of the fundus may be imaged by turning on a fixation LED and asking the patient to look at it. In exemplary embodiments, additional regions of the fundus may be imaged by, for example, turning on a fixation LED and asking the patient to look, for example, to the right of it, left of it, above it, or below it.

In exemplary embodiments, the operator (or the computer) may select which regions of the fundus are to be imaged during, for example, the initial setup phase. For example, the operator may select which fixation LEDs are to be turned on and which (if any) should not be turned on. Then, during the imaging session, after the set of images of a particular region are collected, the software may automatically turn on the next selected LED.

In exemplary embodiments, the various images of the different portions of the fundus may be combined to create an aggregate image of the fundus by e.g., stitching the various images together.

After coarse alignment, the image of the infrared LED may lie somewhere in the patient's pupil. Once the imaging process is initiated, the device may automatically (or semi-automatically) align precisely to the center of the pupil. To accomplish the alignment, the image on one of the cameras 50 is analyzed by the device software to determine the center of the pupil and motors located within the device are driven (horizontally and/or vertically) to align the pupil.

In exemplary embodiments, one of the cameras 50 may image light passing through the left side of lens 32 while a second camera 50 may image light passing through the right side of lens 32. Accordingly, the two cameras 50 may view the pupil from different angles—e.g., about 5, 6, 7, 8, 9, or 10 degrees apart. Accordingly, when the distance from the pupil to the lens 32 changes, the separation between the pupil images on the two cameras 50 changes. To bring the pupil to exactly the correct distance from lens 32, the software within the device determines the difference in horizontal positions between the images on the two cameras 50 and moves the optics toward or away from the pupil until the two images are precisely registered. In this manner, the optics may be correctly aligned to the patient's pupil in three dimensions.

When the optics are initially aligned, light from the LED light sources 14, 16, 18 is reflected from the patient's cornea and passes along the optical axis of the device to fall on the fundus image sensor 46. In exemplary embodiments, this light may not be desirable because it may mask the fundus image. Accordingly, in exemplary embodiments, it may be desirable to prevent this light from reaching the sensor 46. To accomplish this, in exemplary embodiments, the software may be configured to drive a motor that moves the infrared, red, and/or green LED, causing its image to move up or down. For example, if the patient is looking straight ahead or below, the image is made to move down until its bottom edge is tangent to the bottom of the pupil and if the patient is looking upward, the image is moved upward to be tangent to the top of the pupil. As a result of the geometry of the eye, this method may provide optimal (or at least partial) elimination of the corneal reflection.

Once the properly aligned image of the fundus is projected onto sensor 46, the software may be configured to determine the maximum video signal level in the image and adjust the exposure duration of the sensor until the maximum level is acceptable (e.g., about 70%, 75%, 80%, 85%, or 90% of the highest level that the sensor can deliver).

In exemplary embodiments, the software of the device may be configured to focus the image of the fundus on the sensor 46. For example, in exemplary embodiments, the software may be configured to control a motor that swings a reticle 24 into the optical path between lenses 22 and 26. In exemplary embodiments, the reticle may be approximately in the back focal plane of lens 26 so light from it is approximately collimated when it arrives at the patient's eye, thereby forming an image of the reticle on the patient's retina. In embodiments, the sharpness of focus of this image may depend upon the patient's refractive error, but the focusing method being described here may be insensitive (or at least not sufficiently sensitive) to the sharpness of that image. The reticle 24 consists of an opaque surface comprising a plurality of holes (see, e.g., FIG. 4). When inserted into the optical path, an image of the fundus appears as a pattern of bright spots.

In exemplary embodiments, parallel plane shifter 38 may be a piece of flat glass about 0.50 inches thick. The parallel plane shifter 38 may be mounted in a holder in such a way that the axis perpendicular to its surface is offset about 9 degrees (e.g., 7, 8, 9, 10, 11, or 12 degrees) from the optical axis of the main system. When such a flat piece of glass in introduced into the optical path, its effect varies depending upon which optical rays are considered. For example, if the rays come from an object an infinite distance away, that is, if the rays are collimated, then all of the rays through the parallel plane shifter 38 are bent through the some angle by refraction at the first surface they encounter and are bent precisely back the other way when the exit the parallel plane shifter 38. In this case, if the light passing through parallel plane shifter 38 were collected to form an image of the object, and if the angle between the optical axis and the surface of the parallel plane shifter 38 were to change, the image of the object would not move. All that happens is that a partially different set of rays from the object would form the image. The image itself would not move. However, if the object that is considered the source of the rays is not an infinite distance away, the angles of refraction are not equal for all rays. In this case, if the light passing through parallel plane shifter 38 forms an image of the non-distant object and the angle between the optical axis and the surface of parallel plane shifter 38 were to change, the image would move. It would move as a function of the thickness and index of refraction of parallel plane shifter 38, the change in angle, and the distance of the object from the lens.

In exemplary embodiments, the parallel plane shifter 38 may be mounted in such a way that a motor can cause it to rotate about the optical axis of the device. For example, in an embodiment, since the axis perpendicular to its surface is tilted 9 degrees from the optical axis, when the parallel plane shifter 38 rotates about 180 degrees, its perpendicular axis is tilted 9 degrees in the opposite direction. The approximately 180 degree rotation of parallel plane shifter 38 causes the pupil image to move across the sensor in a direction determined by the change in angle of parallel plane shifter 38. Thus, when the parallel plane shifter 38 is rotated about 180 degrees, the image of the patient's pupil moves across the aperture 42. To correctly focus the fundus image on the sensor, the parallel plane shifter 38 is rotated to one position, such that the center of the image of the pupil is displaced horizontally from the center of the aperture 42. A fundus image is captured and then the parallel plane shifter 38 is rotated about 180 degrees, so that the aperture 42 passes light from the other side of the patient's pupil, and another image is captured. If the image of the fundus is in perfect focus, the image would not move because the motion of the pupil image across the aperture 42 merely selects different rays passing through the pupil to form the fundus image. However, if the image of the fundus is not in focus, that is, if the rays from it are not collimated when they enter lens 54, then the fundus image will move when parallel plane shifter 38 rotates, and the image will move in a direction and with a magnitude that indicates the degree of defocus. In exemplary embodiments, the software may be configured to register the two images of the fundus, one taken through each side of the pupil, determine the direction and size of the shift between the two images, and drive the entire assembly 52 to correct for the error in registration. This process is iterated, as necessary, until there is no (or substantially no) motion between the two fundus images. In this manner, the fundus image is in correct focus. In exemplary embodiments, the parallel plane shifter may be mounted on a gimbal assembly configured to allow the parallel plane shifter to change angles with respect to the optical axis (e.g., see FIG. 5).

As discussed elsewhere, in exemplary embodiments, the parallel plane shifter may be mounted and tilted so that the perpendicular axis of the parallel plane shifter's surface is tilted approximately 9 degrees from the optical axis, and in such a way that when the assembly is rotated through 180 degrees the axis of the parallel plane shifter was tilted approximately 9 degrees away from the optical axis in substantially the opposite direction.

Figure 5:
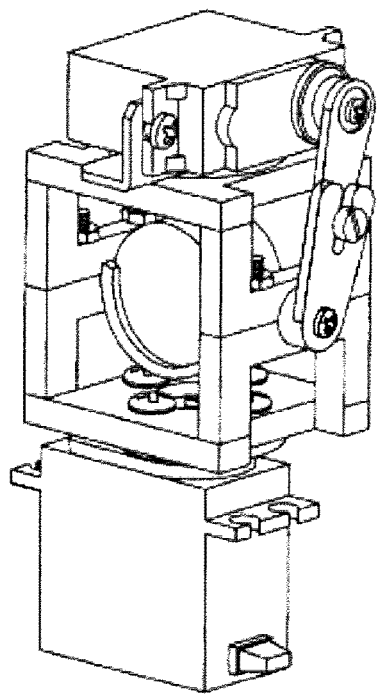
FIG. 5 is an exemplary embodiment of a method for mounting a parallel plane shifter within a device for imaging an ocular fundus.

FIG. 5 is an exemplary embodiment of a method for mounting a parallel plane shifter within a device for imaging an ocular fundus. In FIG. 5, the parallel plane shifter is mounted using a gimbal. In this configuration, two motors may be mounted, one at the top and the other at the bottom of the assembly, with the parallel plane shifter mounted between them. The bottom motor may be configured to cause the parallel plane shifter to rotate about a vertical axis and the top motor may be configured to cause it, through a plurality of linked arms, to rotate about a horizontal axis. In exemplary embodiments, the angle of the motors may be sensed through an angular feedback loop for e.g., accuracy of positioning. In this manner, it may be possible to drive the parallel plane shifter to virtually any angle.

In exemplary embodiments, the processes described above may be performed while the LED light source 18 (IR or near IR LED) is turned on. During all the alignment and focusing steps. LED light source 18 may be illuminated at a relatively low level. Then, after alignment and focus are correct, the intensity of LED light source 18 may be increased for the duration of the exposure that had been computed as described above, the sensor may be activated for that duration, and an image collected, accordingly. In exemplary embodiments, seven additional images may then be captured under the same (or substantially similar) conditions, following each other. In exemplary embodiments, the eight images may be registered and averaged to produce a single, higher quality image. Since near infrared light reflects strongly from all components of the ocular fundus, images taken in near infrared may have inherently low contrast. Accordingly, in exemplary embodiments, to enhance the visibility of fundus features, the images may be "stretched" in software, that is, the darkest regions may be driven to zero brightness, the brightest regions may be driven to the highest possible brightness, and the brightness of all regions in between may be linearly interpolated. When this is performed on low contrast images, they appear noisy. Averaging a group of them may provide some and/or significant improvement.

After the initial eight images are collected, the parallel plane shifter 38 is rotated 180 degrees, moving the image of the patient's pupil to the other side of the optic axis, and another set of eight images are captured, registered, and processed. Because these two sets of images are taken through opposite sides of the pupil, they constitute a stereo pair, which can be viewed to see and measure the relative depth of features such as the optic nerve head.

After the near-infrared images are collected, the infrared LED 18 is turned off and the red LED 16 and the sensor are turned on for an exposure duration that is a fixed percentage of the infrared exposure. In exemplary embodiments, the percentage may be set based on past experience with the relative sensitivity of the camera and reflectance of the fundus in infrared vs. red light. The software may inspect the image and if the brightest region is less than 80% of the maximum usable value, the exposure may be increased proportionately and if the brightest region is saturated, the exposure may be reduced. Then the parallel plane shifter 38 is rotated 180 degrees and a second image is collected. These two images form a stereo pair under red illumination. The process is then repeated for the green LED.

In exemplary embodiments, stereo imaging may provide the ability to visually examine and to quantify the three-dimensional shape of the fundus. For example, a tumor growing in the retina may be invisible in a non-stereo image but can be seen and mapped if imaged as a stereo pair. Similarly, changes in depth over time, such as the growth of a tumor, can be more easily detected and quantified.

For example, stereo fundus imaging may be used in the detection of glaucoma and/or the monitoring of its treatment. In the region of the fundus called the optic disk, or the optic nerve head, the approximately one million nerve fibers carrying signals from photoreceptors in the retina gather together and exit the eyeball to form the optic nerve. These nerve fibers and their accompanying support structures, along with blood vessels, fill most of the volume of the region of the optic disk. Glaucoma causes the deaths of the cell bodies of some of these optic nerve fibers, and the nerve fibers subsequently atrophy, reducing the volume of tissue in the optic disk. The result is an increase in the "dent," called "cupping," of the disk. Stereo imaging of the disk helps provide the information necessary to visualize and/or to measure the degree of this cupping. A thin transparent membrane lies over the entire surface of the retina. Certain pathologies cause this membrane to break and partly peel away from the retina. Such a detached membrane is almost impossible to identify without a stereo image, but can more easily be detected when viewing a stereo pair.

As discussed elsewhere herein, the LEDs for illuminating the eye may be turned on and off individually and sequentially. To collect a standard, simultaneous color image, the scene may be illuminated with white light, and the pixelated sensing surface is overlaid with an array of color filters. For example, the filters typically are arranged such that about half the pixels are covered with filters that pass only green light, about one quarter with filters that pass only red light, and the remaining quarter with filters that pass only blue light. However, using sequential color, the scene is illuminated with, for example, red light, an image is collected, then for example, with green light and an image is collected, and then, for example, blue light and an image is collected. The sequential procedure requires more time but, for a given sensor pixel density, it may produce images for which resolution is greater. In exemplary embodiments, the resolution may be significantly greater (e.g., 25%, 30%, 35%, 40%, 45%, 50%, 60%, 70%, 80%, 90%, or 100% greater) than a comparable simultaneous color image.

Additionally, in exemplary embodiments, when imaging the retina, it may be desirable to make certain features more highly visible. Since different features may absorb certain wavelengths of light more strongly than others, the visibility of those features can be enhanced by selecting the wavelengths of the light illuminating and therefore being reflected by the fundus. Using standard (simultaneous) color imaging, the wavelength pass-bands of the individual filters in the array that covers the sensing pixels determine the wavelengths that are sensed, and it is difficult and expensive to select or vary those pass-bands. However, using sequential color, the different wavelength bands can be easily selected, for example, by choosing LEDs that emit the desired wavelength bands or by using a white light source and interposing color filters between the source and the eye.

Different wavelengths may also be absorbed differently by different retinal layers. For example, green light may be strongly absorbed by features near the surface of the retina while red light and near infrared light may penetrate more deeply. Therefore, using sequential color, images collected with different illumination wavelengths may represent features at different depths in the retina. For example, images collected under green light may reveal surface features, such as the surface membrane and surface blood vessels, while infrared light may reveal pigments that lie deep in the retina.

Generally, standard color images are collected using red, green, and blue light. However, in exemplary embodiments, the camera described herein may omit the blue light from the imaging process. Blue light may be strongly absorbed by the media of the eye through which light has to pass in its path from the front surface of the cornea to the surface of the retina, and as a consequence, images collected under blue illumination may be dark unless a longer exposure is used. The extended exposure time however, results in eye movements which, in turn, may blur the image). Additionally, there may be very little information in a fundus image taken under blue illumination that is not also present in an image taken under green illumination. Accordingly, in exemplary embodiments, there may be little gain in using blue light if green light is being used.

Additionally, because there are numerous lenses in the imaging system, many surfaces exist from which light may be reflected. These reflections have two undesirable consequences. One, that imaging light is lost so exposures have to be longer, and two, that these reflections can fall on the image sensing surface and degrade the visibility of the fundus features. Accordingly, in exemplary embodiments, it may be desirable to minimize or at least reduce these reflections by e.g., applying anti-reflection coatings to the optical surfaces, and the broader the range of wavelengths to be affected, the more expensive is the application of these coatings may be. Therefore, since blue light adds little to the information in a fundus image but may add significant cost, blue light may not be used in the device.

However, blue light does contribute to the overall color image of the fundus. For example, in an experiment, a set of color fundus images was collected using a high-quality standard fundus camera (white illumination and a standard color image sensor with a filter array). The images for the red, green, and blue "channels" were separated electronically, the blue channel was deleted, and the resulting color (red plus green) image was displayed along with the full color (red, green, blue) image. The two images looked clearly different. However, to compensate for this difference, an additional image was created in which the red and green channels were unchanged but the blue channel of the display device was driven instead by the green image. In this case, the blue pixels were configured to display about 40% of the value of the corresponding green channel. This new set of images looked essentially indistinguishable from the standard, full color (red, green, blue) set. Although the blue pixels were driven at about 40% of the value of the corresponding green channels, in exemplary embodiments, the blue pixels may be driven at about 30%, 35%, 36%, 37%, 38%, 39%, 40%, 41%, 42%, 43%, 44%, 45%, or 50% of the value of the corresponding green channels.

In exemplary embodiments, the light to illuminate the fundus may be derived from a tungsten filament halogen bulb and the light may be passed through a motor-selectable filter to render the desired color of illumination. For example, in embodiments, the device may use a near-infrared pass filter, a green pass filter and a red pass filter. In exemplary embodiments, the generated light may pass through one of the filters and the length of the exposure to green light, for example, may be the time required for moving the filter motor so that the green filter replaces the infrared one, then taking the image, then moving the infrared filter back into position. This process may expose the patient's eye to a significantly longer green (or red) light exposure (e.g., about 50, 55, 60, 65, or 70 milliseconds per image). In exemplary embodiments, it may be desirable to reduce the exposure time. Accordingly, in exemplary embodiments, the device may use color specific LEDs like those illustrated in FIG. 1. In this case, the individual LEDs (or LED sets) may be turned on only during the exposure itself, thereby limiting the patients exposure to the light to about e.g., 15 milliseconds (e.g., 5, 10, 15, 20, 25, 30, 35, 40 milliseconds). In exemplary embodiments, this approach may result in greater comfort for the patient and less time for the patient's pupil to redilate after each image set.

In exemplary embodiments, the device may correct for potential problems introduced by eye movements during the focusing of the fundus by obtaining images from both sides of the pupil simultaneously. In exemplary embodiments, during focusing, an assembly consisting of a silvered right-angle prism, serving as two mirrors at right angles to each other and each at 45 degrees to the optical axis, two cameras and a camera lens for each camera, is moved into the optical path between lenses 36 and 54. In operation, this assembly may be configured to deflect the light that would have formed a fundus image on the sensor 46 and instead forms a fundus image on each of the two cameras. If the fundus image is correctly focused, the two images lie in particular positions with respect to each other, and the departure from those positions indicates the direction and amount of motion needed to achieve correct focus. That is, the positions of the "raw" images of the fundus itself are used to determine focus. Eye movements no longer perturb the measurement because the two images are collected simultaneously.

In exemplary embodiments, an image of the holes in the reticle 24 may be formed on the fundus and the positions of those shadows may be compared, instead of using images of the fundus itself. In exemplary embodiments, this method may have several advantages. First, moving a reticle 24 in or out of the optical path may be easier and less costly than moving an assembly containing a prism, two lenses and two cameras. Second, when regions of the fundus are to be imaged that contain few or no bold features (such as large blood vessels), the images of the holes in the reticle 24 can be used because it is bold and the same regardless of its location on the fundus.

In exemplary embodiments, when a fundus image is to be collected, after focusing has been completed, the focusing assembly described in the preceding paragraphs may be withdrawn from the optical path and an aperture smaller than the image of the patient's pupil may be physically inserted into the optical path so that it lies on one side of the pupil image. An image of the fundus may then be collected. Then the aperture may be shifted to the other side of the pupil and a second image may be collected. These two images form a stereo pair. In exemplary embodiments, the aperture 42 may be built into camera lens 54 and may be conjugate with the patient's pupil. The aperture may be smaller than the image of the pupil, and lie on the optical axis of the instrument. Instead of moving the aperture, in exemplary embodiments, the parallel plane shifter 38 may displace the image of the patient's pupil so that the aperture A is stationary and the pupil image moves across it. In exemplary embodiments, this may be advantageous because camera lens 54 may be a standard of-the-shelf lens and therefore far less expensive than lens designs which require the aperture to move. Additionally, this type of structure may allow the fundus camera to be used as an autorefractor without additional hardware costs.

In the eye care field, the term refraction refers to the process of determining the optical correction, for example, the optical characteristics of spectacle lenses, that may be required to provide the patient with as good vision as possible (or at least improved vision). Autorefractors are commonly used to provide corrections. In operation, a patient looks into the autorefractor and sees a target. The instrument automatically adjusts an optical system that the patient is actually looking through while measuring the sharpness of the image that lies on the patient's retina until the image is as sharp as it can get. In most instruments, the patient then sees the target through the determined correction, and the result can be used either as a prescription for glasses or as a starting point for further manual refraction.

In exemplary embodiments, the device for imaging the fundus may also provide autorefraction. For example, the patient may look straight ahead into the device at the central fixation light discussed above. Using near infrared light from light source 18, the device automatically aligns itself precisely with the pupil, sets the exposure duration, as described above, and sets the fundus focus assembly at the position it would find if the patient has zero refractive error. The reticle 24 is moved into the optical path and a series of fundus images is collected (e.g., 12 images), each with the parallel plane shifter 38 rotated about 15 degrees beyond its previous position. These twelve images are then registered. Each registration produces two values, the horizontal and the vertical distance through which an image must be shifted to register with the previous ones. If there were no noise or other sources of variability, each point of this set of 12 points would lie on an ellipse in two-dimensional space. The size of the major axis of the ellipse would be directly proportional to what is defined as the spherical power of the eye, the difference in size between the major and minor ellipses would be directly proportional to what is defined as the cylindrical power or astigmatism of the eye, and the angle of the ellipse with respect to a horizontal line perpendicular to the optical axis of the instrument is defined as the angle of the cylinder or astigmatism.

Cataracts are regions of the eye lens that, through injury or the accumulation of tiny insults over a lifetime, have lost their orderliness, and as a result, scatter light. Cataracts do absorb a small portion of the light passing through them, but, in general, that absorption has a negligible effect on vision (for example, sunglasses absorb light without significantly impairing vision). It is believed that the scattering of light causes the deleterious effects of cataracts. Therefore, to measure and evaluate cataracts, it is necessary to measure the degree to which they scatter light.

Figure 6:
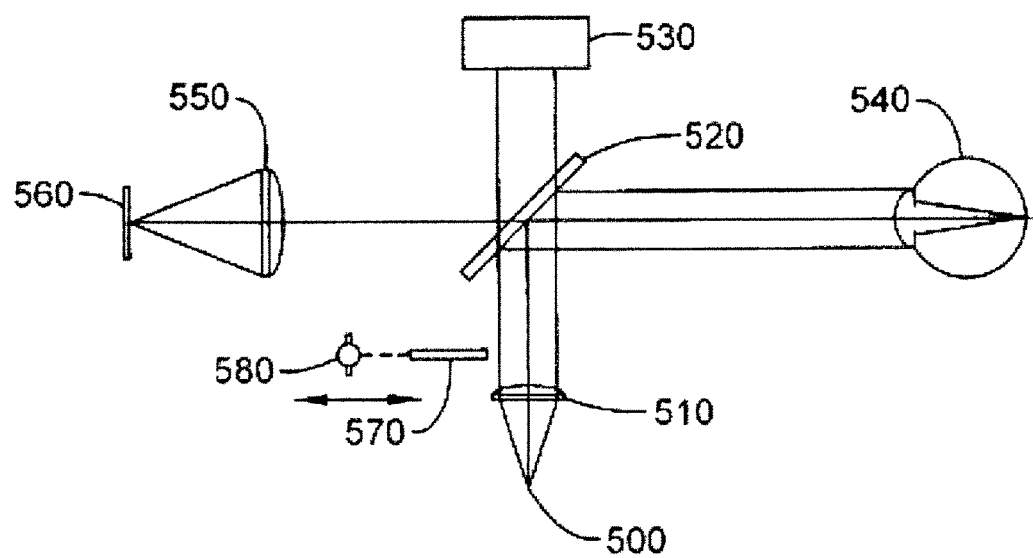
FIG. 6 is a schematic diagram of an exemplary embodiment of a device that may be used to measure cataracts.

FIG. 6 is a schematic diagram of an exemplary embodiment of a device that may be used to measure cataracts. Light from a light source 500 (e.g., an infrared or near infrared LED source), is collimated by lens 510 such that a portion of the light passes through a beamsplitter 520, and is captured in a light trap 530 and a portion of the light is reflected from beamsplitter 520 and is incident on the eye 540. Some of that light passes through the pupil and the refractive surfaces of the eye forms an image of the light source 500 on the retina.

Some of the light reflected from the image of light source 500 on the retina passes back through the eye 540 along the entry path, through the crystalline lens, pupil, and cornea. A portion of the light passes through beamsplitter 520 and lens 550 forms an image of the back-lit pupil on an image sensor 560. In exemplary embodiments, in the image, the pupil may appear as a clear light disk on a dark background.

If a small region of the eye lens contains cataractous tissue, some of the light passing from the retina toward the pupil may pass through the cataractous tissue and be scattered. As a result, some of that light that would have passed through lens 550 and formed an image of the region of the pupil containing the cataractous tissue may instead be scattered and miss lens 550. Accordingly, the image of that region of the pupil may be somewhat darkened. In exemplary embodiments, the more strongly the region scatters light, the more strongly darkened the image may be.

Figure 7:
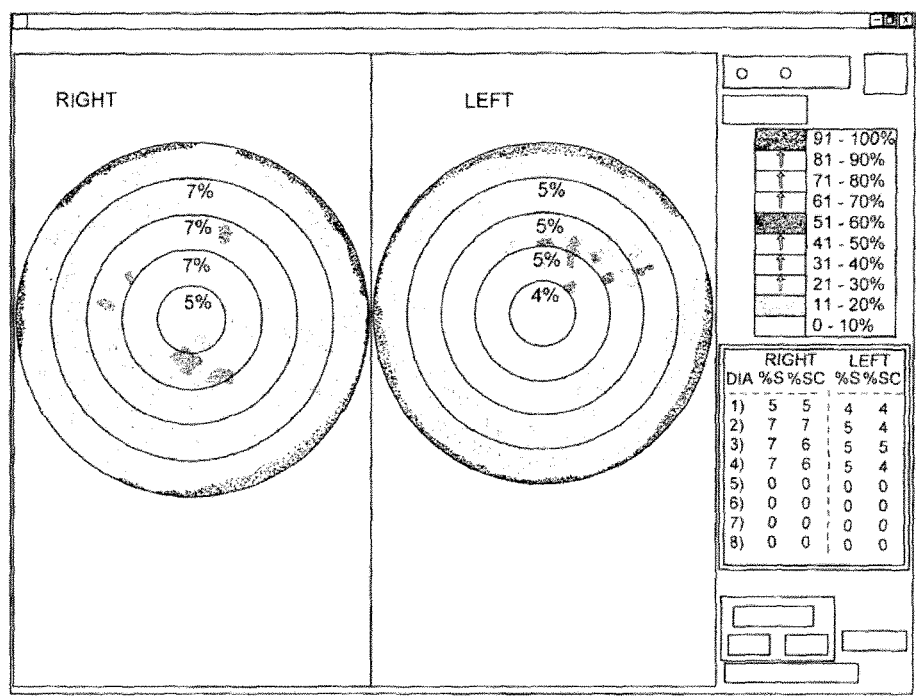
FIG. 7 illustrates an exemplary embodiment of a display screen after capturing and analyzing images of two eyes of a patient containing cataractous tissue.

FIG. 7 illustrates an exemplary embodiment of a display screen after capturing and analyzing images of two eyes of a patient containing cataractous tissue. As illustrated, the densities in these images are pseudocolored, that is, the darkness of each pixel in the original images is displayed as a color according to coding displayed at the upper right of the image. For example, in exemplary embodiments, the central circle drawn on each image may enclose the central region of the pupil one millimeter in diameter, the next larger circle may enclose the central 2 mm diameter region, etc. The numerical value in each region identifies the amount of scatter over that region, as a percentage, where 100% is the maximum possible scatter. The first column for each eye in the table at the lower right of the figure is simply a listing of the same percent numbers. The second column of percentages for each eye are those of the first columns but corrected for the Stiles-Crawford effect. In particular, the photosensors in the human eye that provide high resolution vision, are called cones. Cones have fairly strong directional sensitivity, so that, for example, they are as much as four times more sensitive to light passing through the center of the pupil than to light passing near the edge of a dilated pupil. This phenomenon is referred to as the Stiles-Crawford effect. Therefore, light scattered from a cataractous region at the center of the pupil will have a stronger deleterious effect than light scattered from the edge of the pupil.

In exemplary embodiments, these percentages may be computed in the following manner. First, it may be assumed that the brightest region in an image of the pupil represents a region of the eye lens that has no cataractous tissue. This region may be assigned a percentage of zero. Then it may be assumed that if the scatter in a given region were as strong as it could be, the corresponding region in the image would have zero brightness. All brightnesses between zero and the maximum are then assigned corresponding percentages on a linear scale.

Figure 8:
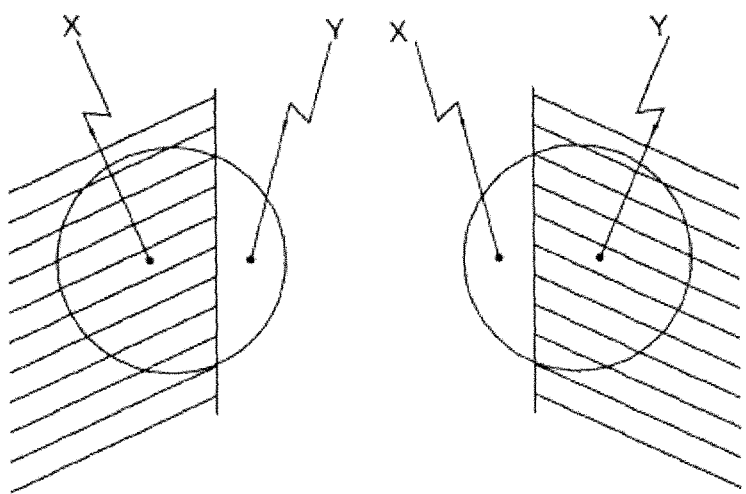
FIG. 8 illustrates an exemplary embodiment of a baffle for use with the exemplary embodiment of the device used to measure catarts.

For some eyes, the assumption in that procedure that the brightest region in the image represents a region of zero scatter may be incorrect. In fact, it may never be quite correct because every region of even the clearest of eye lenses may scatter some light, and in some eyes, there may be no region that does not scatter a significant amount of light. To correct for this assumption (see, e.g., FIG. 8), the following procedure is performed. First, a moveable baffle 570, is moved into the optical path by motor 580 and an image is collected when the baffle is in a position to block the light from entering a little more than half of the pupil, as illustrated by the left portion of FIG. 8. Then the baffle is moved to block light entering the other side of the pupil, as illustrated in the right portion of FIG. 8 and another image is collected. Finally, the baffle is completely removed from the optical path and the system behaves as described above. The brightness of the image of a point in the region marked "X" will have a value that depends on how strongly the light from the retina is scattered at that point. The brightness at point "y" will have a value that depends on how strongly the light from the retina is scattered at that point but its brightness will also be increased by any light scattered directly back from the cataractous region to the sensor.

The scatter at the eye lens of light from the retina is herein referred to as "forward scatter" and the scatter from the eye lens directly back toward the instrument is herein referred to as "back scatter." If a (hypothetical) eye lens actually produced zero scatter, then the brightnesses of region "x" and region "y" would be identical. If the brightness of region "y" is greater than "x," then the amount that it is greater is proportional to the amount of backscatter.

In other words, light that enters the pupil through the exposed (right) side forms an image of the small light source on the retina, the light then emerges from the entire pupil and forms an image on the image sensor. The light forming the image of the left side of the pupil consists of light scattered from the retina. Light forming the image of the right side of the pupil also contains light scattered from the retina, but in addition, if there is cataractous tissue behind the right side of the pupil, its image contains light that is scattered directly from the cataractous tissue. That is, the light forming the image of the right side of the pupil is the sum of light from the retina and light from the cataract. Similarly, when the baffle is moved to block light that would have hit the right side of the pupil, the image of the left side contains light both from the retina and from any cataractous tissue on the left side of the pupil.

Utilizing the three pupil images, one with no blocker and the two with the blocker, substantially all of the pupil has been imaged with light only from the retina—Ir(x,y) and also light scattered directly from any cataractous tissue—IC(x,y). A new image, or map, can be constructed such that the points (x,y) is given the value V=IC(x,y)−Ir(x,y). The value V at the (x,y) points are a measure of the intensity of the light scattered directly from cataractous tissue to the image sensor, the so-called backscatter. In other words, to compute the amount of backscatter at a point in the pupil, the value when that point was not directly illuminated is subtracted from its value when the point was directly illuminated.

This procedure yields a mapping of the strength of backscatter at points throughout the pupil. However, it is the light scattered by the lens at each point that impinges on the retina and causes degradation in vision. Fortunately, the strength of scatter towards the retina at any point in a scattering medium is highly correlated with the strength of backscatter at the same point. Therefore, the mapping of backscatter described above also provides a mapping of the scatter that impairs vision.

While exemplary embodiments have been shown and described herein, it will be obvious to those skilled in the art that such embodiments are provided by way of example only. It is intended that the following claims define the scope of the invention and that methods and structures within the scope of these claims and their equivalents be covered thereby.

What is claimed is:

1. A fundus camera for photographing a fundus of an eye, the fundus camera comprising:
   an optical path;
   at least one imaging sensor;
   an assembly comprising an IR light source, a red light source, and a green light source, wherein the assembly is configured to be movable in at least one axis so as to be individually alignable with the optical path to obtain images of the fundus;
   a plurality of fixation lights configured to orient the fundus in varying positions as a result of a eye's changed direction of gaze;
   a processor configured to control the fundus camera such that during operation, the fundus camera automatically obtains a composite image of the fundus by:
   orienting the IR light source with the optical axis of the camera;
   illuminating the plurality of fixation lights sequentially;
   obtaining narrow bandwidth images of the fundus corresponding to the plurality of fixation lights;
   orienting the red light source with the optical axis;
   illuminating the plurality of fixation lights sequentially;
   obtaining narrow bandwidth images of the fundus corresponding to the plurality of fixation lights;
   orienting the green light source with the optical axis;
   illuminating the plurality of fixation lights sequentially;
   obtaining narrow bandwidth images of the fundus corresponding to the plurality of fixation lights;
   stitching the resulting narrow bandwidth images into a composite image of the fundus;
   wherein the narrow bandwidth images are stereo images.

2. A fundus camera for photographing a fundus of an eye, the fundus camera comprising:
   an optical path;
   at least one imaging sensor;
   an assembly comprising an IR light source, a red light source, and a green light source, wherein the assembly is configured to be movable in at least one axis so as to be individually alignable with the optical path to obtain images of the fundus;
   a plurality of fixation lights configured to orient the fundus in varying positions as a result of a eye's changed direction of gaze;
   a processor configured to control the fundus camera such that during operation, the fundus camera automatically obtains a composite image of the fundus by:
   illuminating a first of the plurality of fixation lights;
   orienting the IR light source, the red light source, and the green light source with the optical axis, sequentially;
   obtaining at least one narrow bandwidth image of the fundus corresponding to each of the IR light source, the red light source, and the green light source;
   illuminating a next of the plurality of fixation lights;

orienting the IR light source, the red light source, and the green light source with the optical axis, sequentially;

obtaining at least one narrow bandwidth image of the fundus corresponding to each of the IR light source, the red light source, and the green light source;

stitching the resulting narrow bandwidth images into a composite image of the fundus;

wherein the narrow bandwidth images are stereo images.

3. The fundus camera of claim 2, wherein the fundus camera is configured to measure pallor by:

selecting a field of the composite image;

for each of the plurality of pixels within the field, calculating pallor as (R−G)/(R+G);

wherein R is the value of a particular pixel obtained while the optical axis was illuminated by the red light source or IR light source and G is the value of a corresponding pixel obtained while the optical axis was illuminated by the green light source; and displaying the resulting image as a pseudocolored image.

4. The fundus camera of claim 2, wherein the fundus camera is configured to measure changes in the 3-dimensional shape of the optical disk by:

selecting a field of the composite image comprising the optic disk;

for each of the plurality of pixels within the field, calculating pallor as (R−G)/(R+G);

wherein R is the value of a particular pixel obtained while the optical axis was illuminated by the red light source or IR light source and G is the value of a corresponding pixel obtained while the optical axis was illuminated by the green light source; and determining the outline of the optic disk as the portion of the image where the pallor transitions from being less than a predetermined threshold to being greater than a predetermined threshold; and displaying the resulting outlined portion of the image.

5. The fundus camera of claim 2, wherein the fundus camera is configured to measure macular pigment density by:

identifying a first image that includes the macula under IR illumination;

identifying a second image that includes the macula under green illumination;

computing the intensity of the infrared image divided by the intensity of the green image for each pixel within the images; and displaying the resulting ratios as a pseudocolored image map.

6. The fundus camera of claim 2, wherein the fundus camera comprises seven fixation lights.

7. The fundus camera of claim 2, wherein the processor is configured to analyze the narrow bandwidth images in substantially real time to determine whether a replacement image is required.

8. The fundus camera of claim 2, wherein the image stitching is performed, at least in part, by calculating a variance of the pixels in a pixel matrix in an image and comparing a cross-correlation to an adjacent image to determine an overlap.

9. The fundus camera of claim 2, wherein the imaging sensor has a field of view of less than 25 degrees.

10. The fundus camera of claim 2, wherein the fundus camera is configured to detect a cataract by quantifying the amount of light scatter in the lens of the eye.

11. The fundus camera of claim 10, further comprising a baffle movable from a position in which the baffle covers more than a first half of the pupil to a position where the baffle covers more than a second half of the pupil and then to a position where the baffle is completely removed from the optical path to enable the at least one processor to differentiate back scatter from forward scatter.

12. The fundus camera of claim 2, wherein the fundus camera is configured to perform an auto-refraction.

13. The fundus camera of claim 1, wherein the fundus camera is configured to measure pallor by:

selecting a field of the composite image;

for each of the plurality of pixels within the field, calculating pallor as (R−G)/(R+G);

wherein R is the value of a particular pixel obtained while the optical axis was illuminated by the red light source or IR light source and G is the value of a corresponding pixel obtained while the optical axis was illuminated by the green light source; and displaying the resulting image as a pseudocolored image.

14. The fundus camera of claim 1, wherein the fundus camera is configured to measure changes in the 3-dimensional shape of the optical disk by:

selecting a field of the composite image comprising the optic disk;

for each of the plurality of pixels within the field, calculating pallor as (R−G)/(R+G);

wherein R is the value of a particular pixel obtained while the optical axis was illuminated by the red light source or IR light source and G is the value of a corresponding pixel obtained while the optical axis was illuminated by the green light source; and determining the outline of the optic disk as the portion of the image where the pallor transitions from being less than a predetermined threshold to being greater than a predetermined threshold; and displaying the resulting outlined portion of the image.

15. The fundus camera of claim 1, wherein the fundus camera is configured to measure macular pigment density by:

identifying a first image that includes the macula under IR illumination;

identifying a second image that includes the macula under green illumination;

computing the intensity of the infrared image divided by the intensity of the green image for each pixel within the images; and displaying the resulting ratios as a pseudocolored image map.

16. The fundus camera of claim 1, wherein the fundus camera comprises seven fixation lights.

17. The fundus camera of claim 1, wherein the processor is configured to analyze the narrow bandwidth images in substantially real time to determine whether a replacement image is required.

18. The fundus camera of claim 1, wherein the image stitching is performed, at least in part, by calculating a variance of the pixels in a pixel matrix in an image and comparing a cross-correlation to an adjacent image to determine an overlap.

19. The fundus camera of claim 1, wherein the imaging sensor has a field of view of less than 25 degrees.

20. The fundus camera of claim 1, wherein the fundus camera is configured to detect a cataract by quantifying the amount of light scatter in the lens of the eye.

21. The fundus camera of claim 20, further comprising a baffle movable from a position in which the baffle covers more than a first half of the pupil to a position where the baffle covers more than a second half of the pupil and then to a position where the baffle is completely removed from the optical path to enable the at least one processor to differentiate back scatter from forward scatter.

22. The fundus camera of claim 1, wherein the fundus camera is configured to perform an auto-refraction.

* * * * *